(12) United States Patent
Dow

(10) Patent No.: US 6,194,454 B1
(45) Date of Patent: Feb. 27, 2001

(54) CYANO CONTAINING OXAMIC ACIDS AND DERIVATIVES AS THYROID RECEPTOR LIGANDS

(75) Inventor: Robert L. Dow, Waterford, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/514,696

(22) Filed: Feb. 28, 2000

Related U.S. Application Data

(60) Provisional application No. 60/122,119, filed on Mar. 1, 1999.

(51) Int. Cl.[7] .................... A61K 31/275; C07C 255/60; A61P 3/06; A61P 3/04

(52) U.S. Cl. .................. 514/522; 558/413; 558/416; 558/417

(58) Field of Search ............................ 514/522; 558/413, 558/417

(56) References Cited

U.S. PATENT DOCUMENTS

| | | | |
|---|---|---|---|
| 4,069,343 | 1/1978 | Sellstedt et al. | 424/319 |
| 4,554,290 | 11/1985 | Böger et al. | 514/487 |
| 4,766,121 | 8/1988 | Ellis et al. | 514/247 |
| 4,826,876 | 5/1989 | Ellis et al. | 514/535 |
| 4,910,305 | 3/1990 | Ellis et al. | 544/239 |
| 5,061,798 | 10/1991 | Emmett et al. | 544/239 |
| 5,232,947 | 8/1993 | Sato et al. | 514/549 |
| 5,284,971 | 2/1994 | Walker et al. | 562/429 |
| 5,401,772 | 3/1995 | Yokoyama et al. | 514/539 |
| 5,569,674 | 10/1996 | Yokoyama et al. | 514/539 |
| 5,654,468 | 8/1997 | Yokoyama et al. | 560/43 |

FOREIGN PATENT DOCUMENTS 0580550 12/1993 (EP).

OTHER PUBLICATIONS

Casiraghi, G. et al., *J.C.S. Perkin Trans.* 1: 1862–1865 (1980).

Chan, D.M.T. et al., *Tetrahedron Letters*, 39: 2933–2936 (1998).

Steele, R.E. et al., *International Congressional Service* (Atherosclerosis X) 1066: 321–324 (1995).

Stephan, Z.F. et al., *Atherosclerosis*, 126: 53–63 (1996).

Underwood, A.H. et al., *Nature*, vol. 324: pp. 425–429 (1986).

Webb, K.S. & Levy, D., *Tetrahedron Lett.*, 36 (29): 5117–5118 (1995).

Wright, S.W. et al., *OPPI Briefs*, 29 (1): 128–131 (1997).

Yokoyama, N. et al., *Journal of Medicinal Chemistry*, 38 (4): 695–707 (1995).

*Primary Examiner*—Michael G. Ambrose
(74) *Attorney, Agent, or Firm*—Peter C. Richardson; Gregg C. Benson; Jennifer A. Kispert

(57) ABSTRACT

The present invention provides novel compounds of the Formula (I)

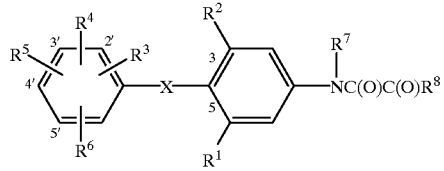

and prodrugs thereof, geometric and optical isomers thereof, and pharmaceutically acceptable salts of such compounds, prodrugs and isomers, wherein $R^1$–$R^8$ and X are as described herein. Pharmaceutical compositions containing such compounds, prodrugs, isomers or pharmaceutically acceptable salts thereof, and methods, pharmaceutical compositions and kits for treating obesity, hyperlipidemia, thyroid disease, hypothyroidism and related disorders and diseases such as diabetes mellitus, atherosclerosis, hypertension, coronary heart disease, hypercholesteremia, depression and osteoporosis are also provided.

45 Claims, No Drawings

CYANO CONTAINING OXAMIC ACIDS AND DERIVATIVES AS THYROID RECEPTOR LIGANDS

CROSSREFERENCE TO RELATED APPLICATION

This application claims priority from U.S. Provisional Patent Application No. 60/122,119 filed Mar. 1, 1999, the benefit of which is hereby claimed under 37 C.F.R. §1.78 (a)(3).

FIELD OF THE INVENTION

The present invention relates to novel thyroid receptor ligands and, more particularly, relates to novel cyano containing oxamic acids, and derivatives thereof, which are useful in the treatment of obesity, hyperlipidemia, thyroid disease, hypothyroidism and related disorders and diseases such as diabetes mellitus, atherosclerosis, hypertension, coronary heart disease, hypercholesteremia, depression and osteoporosis. Also provided are methods, pharmaceutical compositions and kits for treating such diseases and disorders.

BACKGROUND OF THE INVENTION

It is generally accepted that thyroid hormones, specifically, biologically active iodothyronines, are critical to normal development and to maintaining metabolic homeostasis. Thyroid hormones stimulate the metabolism of cholesterol to bile acids and enhance the lipolytic responses of fat cells to other hormones.

Thyroid hormones also affect cardiac function both directly and indirectly, e.g., by increasing the metabolic rate. For example, tachycardia, increased stroke volume, increased cardiac index, cardiac hypertrophy, decreased peripheral vascular resistance and increased pulse pressure are observed in patients with hyperthyroidism.

Disorders of the thyroid are generally treated with hormone replacement by administering either naturally occurring thyroid hormones or thyromimetic analogues thereof which mimic the effects of thyroid hormones.

Two naturally occurring thyroid hormones, namely, thyroxine or 3,5,3',5'-tetraiodo-L-thyronine (commonly referred to as "$T_4$") and 3,5,3'-triiodo-L-thyronine (commonly referred to as "$T_3$"), are shown below:

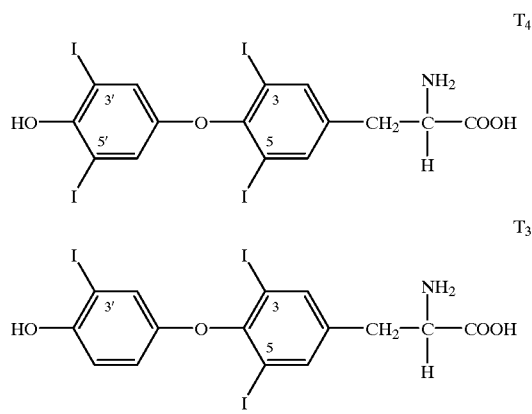

$T_3$ is the more biologically active of the two and, as will be appreciated from the structural formulae provided above, differs from $T_4$ by the absence of the 5' iodine.

$T_3$ may be produced directly from the thyroid gland, or, in peripheral tissues, by the removal of the 5' iodine by deiodinase enzymes. Thyromimetic analogs are often designed to be structurally similar to $T_3$. In addition, naturally occurring metabolites of $T_3$ are known.

As discussed above, thyroid hormones affect cardiac functioning, for example, by causing an increase in the heart rate and, accordingly, an increase in oxygen consumption. While the increase in oxygen consumption may result in certain desired metabolic effects, nonetheless, it does place an extra burden on the heart, which in some situations, may give rise to damaging side effects. Therefore, as is known in the art, such as described by A. H. Underwood et al. in an article published in *Nature*, Vol. 324: pp. 425–429 (1986), efforts have been made to synthesize thyroid hormone analogs which function to lower lipids and serum cholesterol without generating the adverse cardiac effects referred to above.

U.S. Pat. Nos. 4,766,121; 4,826,876; 4,910,305; and 5,061,798 disclose certain thyroid hormone mimetics, namely, 3,5-dibromo-3'-[6-oxo-3(1H)-pyridazinylmethyl]-thyronines.

U.S. Pat. No. 5,284,971 discloses certain thyromimetic cholesterol lowering agents, namely, 4-(3-cyclohexyl-4-hydroxy or -methoxy phenylsulfonyl)-3,5 dibromophenylacetic compounds.

U.S. Pat. Nos. 5,401,772; 5,654,468; and 5,569,674 disclose certain lipid lowering agents, namely, heteroacetic acid derivatives, which compete with radiolabeled $T_3$ in binding assays using rat liver nuclei and plasma membrane preparations.

Certain oxamic acids and derivatives thereof are known in the art, e.g., U.S. Pat. No. 4,069,343 describes the use of certain oxamic acids to prevent immediate type hypersensitivity reactions; U.S. Pat. No. 4,554,290 describes the use of certain oxamic acids to control pests on animals and plants; U.S. Pat. No. 5,232,947 describes the use of certain oxamic acids to improve damaged cerebral functions of the brain; and European Patent Specification published as EP 580,550 discloses certain oxamic acid derivatives as hypocholesteremic agents.

In addition, certain oxamic acid derivatives of thyroid hormones are known in the art. For example, N. Yokoyama et al. in an article published in the *Journal of Medicinal Chemistry*, 38 (4): 695–707 (1995) describe replacing a —$CH_2$ group in a naturally occurring metabolite of $T_3$ with an —NH group resulting in —$HNCOCO_2H$. Likewise, R. E. Steele et al. in an article published in International Congressional Service (*Atherosclerosis* X) 1066: 321–324 (1995) and Z. F. Stephan et al. in an article published in *Atherosclerosis*, 126: 53–63 (1996), describe certain oxamic acid derivatives useful as lipid-lowering thyromimetic agents yet devoid of undesirable cardiac activities.

All of the documents cited herein, including the foregoing, are incorporated by reference herein in their entireties.

SUMMARY OF THE INVENTION

The present invention provides compounds of Formula I:

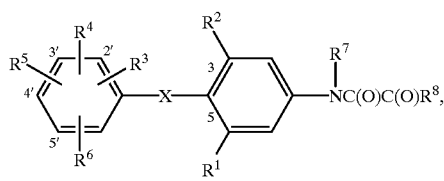

(I)

prodrugs thereof, geometric and optical isomers thereof, and pharmaceutically acceptable salts of said compounds, said prodrugs, and said isomers, wherein:

$R^1$ and $R^2$ are independently halogen, $C_{1-8}$ alkyl, —CN or $C_{1-8}$ perfluoroalkyl; provided that at least one of $R^1$ and $R^2$ is —CN;

$R^3$ is hydrogen or $C_{1-8}$ alkyl;

$R^4$ is halogen, $C_{1-8}$ perfluoroalkyl, $C_{1-8}$ alkyl, $C_{1-8}$ alkanoyl, hydroxy-($C_{1-8}$ alkyl), aryl optionally substituted with Y and Z, aryl-($C_{1-8}$ alkyl), carbocyclic aroyl optionally substituted with Y and Z, $C_{3-10}$ cycloalkyl optionally substituted with Y and Z, or $C_{3-10}$ cycloalkyl-($C_{1-8}$ alkyl);

or $R^4$ is the radical

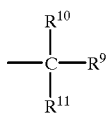

wherein: $R^9$ is hydrogen, $C_{1-8}$ alkyl, aryl optionally substituted with Y and Z, aryl-($C_{1-8}$ alkyl), $C_{3-10}$ cycloalkyl optionally substituted with Y and Z, or $C_{3-10}$ cycloalkyl-($C_{1-8}$ alkyl); $R^{10}$ is —$OR^{14}$; $R^{11}$ is hydrogen or $C_{1-8}$ alkyl; or $R^{10}$ and $R^{11}$ may be taken together with the carbon atom to which they are attached to form a carbonyl group;

$R^5$ is hydroxy, esterified hydroxy or etherified hydroxy;

$R^6$ is hydrogen, halogen, $C_{1-8}$ alkyl or $C_{1-8}$ perfluoroalkyl;

$R^7$ is hydrogen, $C_{1-8}$ alkyl or $C_{1-8}$ perfluoroalkyl;

$R^8$ is —$OR^{12}$ or —$NR^{12}R^{13}$;

$R^{12}$ and $R^{13}$ are each independently hydrogen or $C_{1-8}$ alkyl;

$R^{14}$ is hydrogen, $C_{1-8}$ alkyl or $C_{1-8}$ acyl;

X is O, $S(O)_a$, C=O or $NR^{15}$;

a is 0, 1 or 2;

$R^{15}$ is hydrogen or $C_{1-8}$ alkyl;

Y and Z for each occurrence are independently (a) hydrogen, (b) halogen, (c) trifluoromethyl, (d) —$OCF_3$, (e) —CN, (f) $C_{1-6}$ alkyl optionally substituted with one or more substituents independently selected from the group consisting of halogen, —$OCF_3$, —$CF_3$ and phenyl, (g) $C_{1-6}$ alkoxy, (h) aryl optionally substituted with one or more substituents independently selected from the group consisting of halogen, —$OCF_3$, —$CF_3$, $C_{1-4}$ alkyl and $C_{1-4}$ alkoxy, (i) —$C(O)_2R^{16}$, (j) —$C(O)NR^{16}R^{17}$, (k) —$C(O)R^{16}$, (l) —$NR^{16}C(O)NR^{16}R^{17}$ or (m) —$NR^{16}C(O)R^{17}$; or Y and Z for any occurrence may be taken together to form (a) a carbocycle of the formula —$(CH_2)_b$—, or (b) a heterocycle selected from the group consisting of —$O(CH_2)_cO$—, $(CH_2)_dNH$— and —CH=CHNH—;

b is 3, 4, 5, 6 or 7;

c and d are each independently 2, 3, 4, 5 or 6;

$R^{16}$ and $R^{17}$ for each occurrence are independently hydrogen, $C_{1-6}$ alkyl, $C_{2-6}$ alkenyl, —($C_{1-6}$ alkyl)-$C_{1-6}$ alkoxy, aryl optionally substituted with Y and Z, het optionally substituted with Y and Z, —($C_{1-4}$ alkyl)-aryl optionally substituted with Y and Z, —($C_{1-4}$ alkyl)-heterocycle optionally substituted with Y and Z, —($C_{1-4}$ alkyl)-hydroxy, —($C_{1-4}$ alkyl)-halo, —($C_{1-4}$ alkyl)-poly-halo, —($C_{1-4}$ alkyl)-$CONR^{18}R^{19}$ or $C_{3-10}$ cycloalkyl;

het for each occurrence is a 4-, 5-, 6-, 7- or 8-membered partially or fully saturated, or unsaturated, ring containing from one to four heteroatoms independently selected from the group consisting of N, O and S, and including any bicyclic group in which any of the above heterocyclic rings is fused to a benzene ring or another heterocycle which is a 4-, 5-, 6-, 7- or 8-membered partially or fully saturated, or unsaturated, ring containing from one to four heteroatoms independently selected from the group consisting of N, O and S; and $R^{18}$ and $R^{19}$ for each occurrence are independently hydrogen, $C_{1-6}$ alkyl, $C_{3-10}$ cycloalkyl or aryl optionally substituted with Y and Z.

A preferred group of compounds and pharmaceutically acceptable salts of such compounds, designated the A Group, contains those compounds of Formula I and pharmaceutically acceptable salts of such compounds, as shown above, wherein X is oxygen.

A preferred group of compounds and pharmaceutically acceptable salts of such compounds, of the A Group, designated the B Group, contains those compounds of Formula I and pharmaceutically acceptable salts of such compounds, as shown above, wherein $R^3$ is located at the 2' position, $R^4$ is located at the 3' position, $R^5$ is located at the 4' position and $R^6$ is located at the 5' position.

A preferred group of compounds and pharmaceutically acceptable salts of such compounds, of the B Group, designated the C Group, contains those compounds of Formula I and pharmaceutically acceptable salts of such compounds, as shown above, wherein $R^3$, $R^5$ and $R^7$ are hydrogen, and $R^6$ is hydroxy.

A preferred group of compounds and pharmaceutically acceptable salts of such compounds, of the C Group, designated the D Group, contains those compounds of Formula I and pharmaceutically acceptable salts of such compounds, as shown above, wherein $R^1$ and $R^2$ are each independently —CN, methyl or chloro, provided that at least one of $R^1$ and $R^2$ is —CN.

A preferred group of compounds and pharmaceutically acceptable salts of such compounds, of the D Group, designated the E Group, contains those compounds of Formula I and pharmaceutically acceptable salts of such compounds, as shown above, wherein $R^8$ is —$OR^{12}$.

A preferred group of compounds and pharmaceutically acceptable salts of such compounds, of the E Group, designated the F Group, contains those compounds of Formula I and pharmaceutically acceptable salts of such compounds, as shown above, wherein $R^{12}$ is hydrogen, methyl or ethyl, and $R^4$ is —$CH(CH_3)_2$.

A preferred group of compounds and pharmaceutically acceptable salts of such compounds, of the D Group, designated the G Group, contains those compounds of Formula I and pharmaceutically acceptable salts of such compounds, as shown above, wherein $R^8$ is —$NR^{12}R^{13}$.

A preferred group of the pharmaceutically acceptable salts of the compounds of Formula I, and the prodrugs, geometric and optical isomers thereof, contains those pharmaceutically acceptable salts of the compounds, prodrugs, and geometric and optical isomers wherein the salt is a potassium or sodium salt.

A preferred group of compounds of Formula I, prodrugs and geometric and optical isomers thereof, and pharmaceutically acceptable salts of the compounds, prodrugs and isomers, designated the H Group, includes the specific compounds N-[3-cyano-4-(4-hydroxy-3-isopropyl-phenoxy)-5-methyl-phenyl]-oxamic acid and N-[3-chloro-5-cyano-4-(4-hydroxy-3-isopropyl-phenoxy)-phenyl]-oxamic acid, and the ethyl esters thereof.

A preferred group of the pharmaceutically acceptable salts of the compounds, prodrugs, and geometric and optical isomers of the H Group, designated the I Group, contains those pharmaceutically acceptable salts of the compounds, prodrugs, and geometric and optical isomers wherein the salt is a potassium or sodium salt.

This invention provides methods of treating a condition selected from obesity, hyperlipidemia, thyroid disease, hypothyroidism, diabetes mellitus, atherosclerosis, hypertension, coronary heart disease, hypercholesteremia, depression and osteoporosis, in a mammal (including a human being) which comprise administering to said mammal an effective treating amount of a compound of Formula I, or a prodrug thereof, or a geometric or an optical isomer thereof, or a pharmaceutically acceptable salt of such compound, such prodrug, or such isomer, as described above.

In another aspect, this invention provides methods of treating a condition selected from obesity, hyperlipidemia, thyroid disease, hypothyroidism, diabetes mellitus, atherosclerosis, hypertension, coronary heart disease, hypercholesteremia, depression and osteoporosis, in a mammal (including a human being) which comprise administering to said mammal effective treating amounts of a compound of Formula I, or a prodrug thereof, or a geometric or an optical isomer thereof, or a pharmaceutically acceptable salt of such compound, such prodrug, or such isomer, as described above, and an anorectic agent.

In another aspect, this invention provides methods of treating a condition selected from obesity, hyperlipidemia, thyroid disease, hypothyroidism, diabetes mellitus, atherosclerosis, hypertension, coronary heart disease, hypercholesteremia, depression and osteoporosis, in a mammal (including a human being) which comprise administering to said mammal effective treating amounts of a compound of Formula I, or a prodrug thereof, or a geometric or an optical isomer thereof, or a pharmaceutically acceptable salt of such compound, such prodrug, or such isomer, as described above, and a lipase inhibitor.

In a preferred aspect, this invention provides methods of treating obesity in mammals (including a human being) which comprise administering to said mammal an obesity treating effective amount of compound of Formula I, or a prodrug thereof, or a geometric or an optical isomer thereof, or a pharmaceutically acceptable salt of such compound, prodrug, or isomer, as described above.

In another aspect, this invention provides methods of treating obesity in mammals (including a human being) which comprise administering to said mammal obesity treating effective amounts of a compound of Formula I, or a prodrug thereof, or a geometric or an optical isomer thereof, or a pharmaceutically acceptable salt of such compound, prodrug, or isomer, as described above, and an anorectic agent.

In another aspect, this invention provides methods of treating obesity, in a mammal (including a human being) which comprise administering to said mammal obesity treating effective amounts of a compound of Formula I, or a prodrug thereof, or a geometric or an optical isomer thereof, or a pharmaceutically acceptable salt of such compound, such prodrug, or such isomer, as described above, and a lipase inhibitor.

In another aspect, this invention provides pharmaceutical compositions comprising a compound of Formula I, or a prodrug thereof, or a geometric or an optical isomer thereof, or a pharmaceutically acceptable salt of such compound, prodrug, or isomer, as described above, and a pharmaceutically acceptable vehicle, diluent or carrier.

In another aspect, this invention provides pharmaceutical compositions comprising a compound of Formula I, or a prodrug thereof, or a geometric or an optical isomer thereof, or a pharmaceutically acceptable salt of such compound, prodrug, or isomer, as described above, an anorectic agent and a pharmaceutically acceptable vehicle, diluent or carrier.

In another aspect, this invention provides pharmaceutical compositions comprising a compound of Formula I, or a prodrug thereof, or a geometric or an optical isomer thereof, or a pharmaceutically acceptable salt of such compound, prodrug, or isomer, as described above, a lipase inhibitor and a pharmaceutically acceptable vehicle, diluent or carrier.

In another aspect, this invention provides pharmaceutical compositions for treating a condition selected from obesity, hyperlipidemia, thyroid disease, hypothyroidism, diabetes mellitus, atherosclerosis, hypertension, coronary heart disease, hypercholesteremia, depression and osteoporosis, in a mammal (including a human being) comprising a compound of Formula I, or a prodrug thereof, or a geometric or an optical isomer thereof, or a pharmaceutically acceptable salt of such compound, prodrug, or isomer, as described above, and a pharmaceutically acceptable vehicle, diluent or carrier.

In another aspect, this invention provides pharmaceutical compositions for treating a condition selected from obesity, hyperlipidemia, thyroid disease, hypothyroidism, diabetes mellitus, atherosclerosis, hypertension, coronary heart disease, hypercholesteremia, depression and osteoporosis, in a mammal (including a human being) comprising a compound of Formula I, or a prodrug thereof, or a geometric or an optical isomer thereof, or a pharmaceutically acceptable salt of such compound, prodrug, or isomer, as described above, an anorectic agent, and a pharmaceutically acceptable vehicle, diluent or carrier.

In another aspect, this invention provides pharmaceutical compositions for treating a condition selected from obesity, hyperlipidemia, thyroid disease, hypothyroidism, diabetes mellitus, atherosclerosis, hypertension, coronary heart disease, hypercholesteremia, depression and osteoporosis, in a mammal (including a human being) comprising a compound of Formula I, or a prodrug thereof, or a geometric or an optical isomer thereof, or a pharmaceutically acceptable salt of such compound, prodrug, or isomer, as described above, a lipase inhibitor, and a pharmaceutically acceptable vehicle, diluent or carrier.

In another preferred aspect, this invention provides pharmaceutical compositions for treating obesity in a mammal (including a human being) comprising a compound of Formula I, or a prodrug thereof, or a geometric or an optical isomer thereof, or a pharmaceutically acceptable salt of such compound, prodrug, or isomer, as described above, and a pharmaceutically acceptable vehicle, diluent or carrier.

In yet another aspect, this invention provides pharmaceutical compositions for treating obesity in a mammal (including a human being) comprising a compound of Formula I, or a prodrug thereof, or a geometric or an optical isomer thereof, or a pharmaceutically acceptable salt of such compound, prodrug, or isomer, as described above, an anorectic agent, and a pharmaceutically acceptable vehicle, diluent or carrier.

In yet another aspect, this invention provides pharmaceutical compositions for treating obesity in a mammal (including a human being) comprising a compound of Formula I, or a prodrug thereof, or a geometric or an optical isomer thereof, or a pharmaceutically acceptable salt of such compound, prodrug, or isomer, as described above, a lipase inhibitor, and a pharmaceutically acceptable vehicle, diluent or carrier.

In another aspect, this invention provides kits for the treatment of a condition selected from obesity, hyperlipidemia, thyroid disease, hypothyroidism, diabetes mellitus, atherosclerosis, hypertension, coronary heart disease, hypercholesteremia, depression and osteoporosis which comprise: a first compound, said first compound being a compound of Formula I, or a prodrug thereof, or a geometric or an optical isomer thereof, or a pharmaceutically acceptable salt of such compound, prodrug, or isomer, as described above, and a pharmaceutically acceptable vehicle, carrier or diluent, in a first unit dosage form; a second compound, said second compound being an anorectic agent or a lipase inhibitor, and a pharmaceutically acceptable vehicle, carrier or diluent, in a second unit dosage form; and a container.

In another preferred aspect, this invention provides kits for the treatment of a obesity which comprise: a first compound, said first compound being a compound of Formula I, or a prodrug thereof, or a geometric or an optical isomer thereof, or a pharmaceutically acceptable salt of such compound, prodrug, or isomer, as described above, and a pharmaceutically acceptable vehicle, carrier or diluent, in a first unit dosage form; a second compound, said second compound being an anorectic agent or a lipase inhibitor, and a pharmaceutically acceptable vehicle, carrier or diluent, in a second unit dosage form; and a container.

Unless otherwise provided herein:

"acyl" means an organic radical derived from an organic acid by the removal of the hydroxyl group, including, as the case may be, for example, acetyl, $C_{1-8}$ alkanoyl, carbocyclic aryl-$C_{1-8}$ alkanoyl or carbocyclic aroyl;

"alkanoyl" means a univalent or bivalent acyl radical formed by removal of hydroxyl from the carboxyl group which replaced the methyl group at the end of the main chain of the acyclic hydrocarbon; "$C_{1-8}$ alkanoyl" includes, as the case may be for example, acetyl, propionyl, butyryl or pivaloyl;

"alkanoylamino" of "$C_{1-8}$ alkanoylamino" includes, as the case may be, for example, acetamido or propionamido;

"alkoxy" means an alkyl radical which is attached to the remainder of the molecule by oxygen, including as the case may be, for example, methoxy, ethoxy, propoxy, isopropoxy or butoxy;

"alkoxycarbonyl" of "$C_{1-8}$ alkoxycarbonyl" preferably contains one to four carbon atoms in the alkoxy moiety and includes, as the case may be, for example, methoxycarbonyl, ethoxycarbonyl, propoxycarbonyl and isopropoxycarbonyl;

"alkyl" means a straight or branched hydrocarbon chain radical, including as the case may be, for example, methyl, ethyl, n-propyl, isopropyl, n-butyl and the like;

"aroyl" means aryl acyl, including, as the case may be, for example, benzenesulfonyl, benzoyl and naphthoyl; preferably benzoyl and benzoyl substituted on the benzene ring by $C_{1-8}$ alkyl, $C_{1-8}$ alkoxy, halogen or trifluoromethyl;

"aryl" includes carbocyclic aryl and heterocyclic aryl, and is preferably phenyl optionally substituted by one or two of $C_{1-8}$ alkyl, $C_{1-8}$ alkoxy, hydroxy, $C_{1-8}$ alkanoyloxy, halogen, trifluoromethyl, cyano, $C_{1-12}$ alkanoylamino or $C_{1-8}$ alkoxycarbonyl; "aryl" of "aryl-$C_{1-8}$ alkyl" is preferably benzyl or phenethyl optionally substituted by one or two of $C_{1-8}$ alkyl, $C_{1-8}$ alkoxy, hydroxy, $C_{1-8}$ alkanoyloxy, halogen or trifluoromethyl;

"carbocyclic" (carbocycle) means an unsaturated, or a partially or fully saturated, ring having only carbon atoms in its nucleus, including, as the case may be, an aryl (an organic radical derived from an aromatic hydrocarbon by the removal of one atom, e.g., phenyl from benzene, also including, for example, naphthyl);

"carbocyclic aryl" includes, as the case may be, for example, optionally substituted phenyl or optionally substituted naphthyl;

"cycloalkane" means a saturated, monocyclic hydrocarbon, including, as the case may be, for example, cyclohexane;

"$C_{3-10}$ cycloalkyl" means a monocyclic or polycyclic radical derived from a cycloalkane, including as the case may be, for example, cyclopentyl and cyclohexyl;

"$C_{3-10}$ cycloalkyl-($C_{1-8}$ alkyl) includes, as the case may be, for example, 1- or 2-(cyclopentyl or cyclohexyl)ethyl, 1-, 2- or 3-(cyclopentyl or cyclohexyl)propyl, or 1-, 2-, 3- or 4-(cyclopentyl or cyclohexyl)butyl;

"esterified hydroxy" means acyloxy, e.g., acyloxy derived from an organic carboxylic acid, preferably $C_{1-12}$ alkanoyloxy, aroyloxy, or aryl-($C_{1-8}$ alkanoyloxy); also, 3,7,12(3α, 5β, 7α, 12α)-trihydroxy-cholan-24-oyloxy (derived from cholic acid), and the like;

"etherified hydroxy" includes, as the case may be, for example, $C_{1-8}$ alkoxy, $C_{1-8}$ alkenyloxy, $C_{5-7}$ cycloalkyloxy, carbocyclic aryl-$C_{1-8}$ alkoxy, tetrahydropyranyloxy, $C_{5-7}$ cycloalkyl-$C_{1-8}$ alkoxy, and the like;

"halo" and "halogen" mean a radical derived from the elements fluorine, chlorine, bromine or iodine;

"heterocyclic" ("heterocycle") means a radical derived from an unsaturated, or a partially or fully saturated, ring of different types of atoms, and includes aromatic and non-aromatic heterocyclic groups containing one or more heteroatoms each selected from O, S and N; examples of heterocyclic groups include, as the case may be, for example, benzimidazolyl, benzofuranyl, benzothiophenyl, benzoxazolyl, furyl, imidazolyl, indolyl, isoquinolyl, isothiazolyl, isoxazolyl, morpholinyl, oxadiazolyl, oxazolyl, piperazinyl, piperidyl, pyranyl, pyrazinyl, pyrazolyl, pyridyl, pyrimidyl, pyrrolyl, quinolyl, tetrahydroisoquinoly, tetrahydroquinolyl, tetrahydrothienyl, tetrazolyl, thiadiazolyl, thiazolyl, thienyl, thiomorpholinyl, thiophenyl and triazolyl; where heterocyclic groups are specifically recited or covered as substituents for the compounds of Formula I, it is understood that, unless specifically noted otherwise, all suitable isomers of such heterocyclic groups are intended;

"heterocyclic aryl" includes, as the case may be, for example, monocyclic heterocyclic aryl, e.g., optionally substituted thienyl, furanyl, pyridyl, pyrrolyl or N—($C_{1-8}$ alkyl)pyrrolyl; optionally substituted thienyl includes 2- or 3-thienyl and 2- or 3-thienyl preferably substituted by $C_{1-12}$ alkyl; optionally substituted furanyl includes 2- or 3-furanyl and 2- or 3-furanyl preferably substituted by $C_{1-12}$ alkyl; optionally substituted pyridyl includes 2-, 3- or 4-pyridyl and 2-, 3- or 4-pyridyl preferably substituted by $C_{1-8}$ alkyl or halogen;

a "hydrate" is a crystalline substance containing one or more molecules of water of crystallization, i.e., a substance containing water combined in the molecular form, and all suitable hydrates are part of the present invention;

"hydroxy-($C_{1-8}$ alkyl)" includes, as the case may be, for example, hydroxymethyl;

"perfluoroalkyl" means that all suitable hydrogen atoms are replaced with fluorine atoms, e.g., perfluoropentyl, $CF_3(CF_2)_3CF_2-$;

"pharmaceutically acceptable" means that the carrier, diluent, vehicle excipients, and/or salt must be compatible with the other ingredients of the formulation, and not deleterious to the recipient thereof;

"pharmaceutically acceptable salts" of the compounds of this invention may be formed of the compound itself, prodrugs, e.g. esters, isomers and the like, and include all of the pharmaceutically acceptable salts which are most often used in pharmaceutical chemistry; for example, salts may be formed with inorganic or organic acids such as hydrochloric acid, hydrobromic acid, hydroiodic acid, carboxylic acids, sulfonic acids including such agents as naphthalenesulfonic, ethanesulfonic, hydroxyethanesulfonic, methanesulfonic ("mesylate"), benzenesulfonic ("besylate") and toluenesulfonic acids, e.g., p-toluenesulfonic ("tosylate"), sulfuric acid, nitric acid, phosphoric acid, tartaric acid, pyrosulfuric acid, metaphosphoric acid, succinic acid, formic acid, phthalic acid, malic acid, maleic acid, lactic acid, ascorbic acid, glycollic acid, gluconic acid, mandelic acid, glutamic acid, aspartic acid, fumaric acid, pyruvic acid, phenylacetic acid, pamoic acid, nicotinic acid, and the like; suitable pharmaceutically acceptable salts also include alkali metal salts (e.g. sodium, potassium salts), alkaline earth metal salts (e.g. magnesium, calcium salts), amine salts (e.g. ammonium, alkylammonium, dialkylammonium, trialkylammonium, tetraalkylammonium, diethanolaminium, tri-ethanolaminium and guanidinium salts); preferred salts include salts of organic acids selected from formic, acetic, trifluoroacetic, propionic, benzoic, citric, maleic, tartaric, methanesulfonic, benzenesulfonic or toluenesulfonic, salts of inorganic acids selected from hydrochloric, hydrobromic, sulfuric or phosphoric, amino acids selected from aspartic and glutamic, and salts of sodium and potassium;

a "polymorph" is a substance that occurs in two or more forms;

a "prodrug" is a drug precursor which, following administration, releases the drug in vivo via some chemical or physiological process (e.g., a prodrug on being brought to the physiological pH or through enzyme action is converted to the desired drug form); exemplary prodrugs upon cleavage release the corresponding free acid, and such hydrolyzable ester-forming residues of the compounds of Formula I include but are not limited to those having a carboxyl moiety wherein the free hydrogen is replaced by ($C_1-C_4$)alkyl, ($C_2-C_7$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N, N—($C_1-C_2$)alkylamino($C_2-C_3$)alkyl (such as b-dimethylaminoethyl), carbamoyl-($C_1-C_2$)alkyl, N,N-di($C_1-C_2$)alkylcarbamoyl-($C_1-C_2$)alkyl and piperidino-, pyrrolidino- or morpholino($C_2-C_3$)alkyl;

a "radical" is a group of atoms that behaves as a single atom in a chemical reaction, e.g., an organic radical is a group of atoms which confers characteristic properties on a compound containing it, or which remains unchanged during a series of reactions;

a "solvate" is a molecular or ionic complex of molecules or ions of a solvent with those of a solute; a "solvate" wherein the solvent is water, forms "hydrates" or hydrated ions, and all suitable solvates are part of the present invention; and "treating," "treat" or "treatment" includes, inter alia, preventative (e.g., prophylactic), palliative and curative treatment.

DETAILED DESCRIPTION OF THE INVENTION

Unless otherwise noted, throughout this document: ° C. is degrees Centigrade, % is percent, Ci is Curies, cm is centimeter or centimeters, DEE is diethyl ether, DMF is dimethylformamide, DMSO is dimethylsulfoxide, EtOH is ethanol, Found is found data, g is gram or grams, h is hour or hours, kg is kilogram or kilograms, L is liter or liters, M is molar (concentration), MeOH is methanol, mg is milligram or milligrams, min is minute or minutes, mL is milliliter or milliliters, mmol is millimole or millimoles, mM is millimolar (concentration), MS is mass spectrum, N is normal (concentration), nM is nanomolar (concentration), psi is pounds per square inch, RT is room temperature, TEA is triethylamine, THF is tetrahydrofuran, $\mu$g is microgram or micrograms, and $\mu$L is microliter or microliters.

As disclosed herein, a compound within the scope of Formula I shall at all times be understood to include all active forms of such compounds, including, for example, the free form thereof, e.g., the free acid or base form and also, all prodrugs, polymorphs, hydrates, solvates, stereoisomers, e.g., diastereomers and enantiomers, and the like, and all pharmaceutically acceptable salts as described above. It will also be appreciated that suitable active metabolites of compounds within the scope of Formula I, in any suitable form, are also included herein.

More specifically, certain compounds suitable for use in the present invention such as, for example, certain compounds of Formula I may have asymmetric centers and therefore exist in different enantiomeric forms. All suitable optical isomers and stereoisomers of such compounds, and mixtures thereof, are considered to be within the scope of the invention. With respect to such compounds, the present invention includes the use of a racemate, a single enantiomeric form, a single diastereomeric form, or mixtures thereof, as suitable. Moreover, such compounds may also exist as tautomers. Accordingly, the present invention relates to the use of all such suitable tautomers and mixtures thereof.

In addition, those skilled in the art will easily recognize that physiologically active compounds which have accessible hydroxy groups are frequently administered in the form of pharmaceutically acceptable esters. The compounds of this invention can be administered as esters, formed on the hydroxy groups. While the mechanism has not yet been investigated and not wishing to be bound by theory, it is believed that such esters are metabolically cleaved in the body, and that the actual drug is the hydroxy compound itself. It is possible, as has long been known in pharmaceutical chemistry, to adjust the rate or duration of action of the compound by suitable choices of ester groups.

Those skilled in the art will understand from this disclosure how to prepare the compounds of the present invention using any suitable known method. Moreover, the reaction SCHEME A of the present description illustrates the preparation of the compounds of the present invention and, unless otherwise indicated, $R^1$, $R^3$, $R^4$ and $R^6$ in SCHEME A are as described above. In addition, the EXAMPLES provided herein, as well as the description of the common intermediate, further illustrate the preparation of the compounds of the present invention.

The subject invention also includes isotopically-labelled compounds, which are identical to those recited in Formula I, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically-labelled compounds of Formula I of this invention and prodrugs thereof can generally be prepared by carrying out the procedures disclosed in SCHEME A and/or in the EXAMPLES below, by substituting a readily available isotopically-labelled reagent for a non-isotopically labelled reagent.

The starting materials for SCHEME A, common intermediates a and a-1 and the Examples of the present description are either commercially available or can be prepared according to methods known to those skilled in the art such as described, for example, in the aforementioned U.S. Pat. Nos. 5,401,772; 5,569,674; and 5,654,468, and European Patent Specification published as EP 580,550.

For example, described immediately below, and also in the Examples provided herein, are methods for preparing various starting materials which those skilled in the art will appreciate as suitable for preparing the compounds of Formula I of the present invention:

(1) 4-chloro-3-cyano-5-methylnitrobenzene: can be prepared utilizing the procedure described by S. W. Wright in an article published in the *OPPI Briefs*, 29(1): 128–131 (1997) or as disclosed in the aforementioned U.S. Pat. Nos. 5,401,772; 5,569,674; and 5,654,468 and the European Patent Specification published as EP 580,550;

(2) 3-cyano-4,5-dichloronitrobenzene: can be prepared using the aforementioned procedures, or as described by G. Casiraghi et al. in an article published in the *J.C.S. Perkin Trans. I:* 1862–1865 (1980)), starting with 3-chloro-2-hydroxybenzaldehyde; and (3) 3-isopropyl-4-methoxyphenol: can be prepared using the conditions described by K. S. Webb and D. Levy in an article published in the *Tetrahedron Lett.*, 36(29): 5117–5118 (1995), starting with 3-isopropyl-4-methoxy-benzene boronic acid.

As discussed above, the compounds of the present invention can be prepared from a common intermediate a as described below

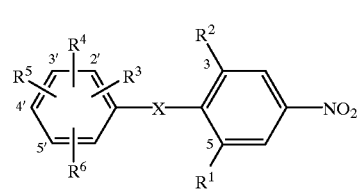

a which itself may be synthesized according to any suitable methods known in the art. More specifically, those skilled in the art will understand based upon the present disclosure how to prepare the common intermediate a wherein X is oxygen, $(SO_2)_a$, C=O, or $NR^{15}$ wherein a and $R^{15}$ are as described above. It is particularly preferred that X is oxygen.

For example, common intermediate a wherein X is oxygen ("a-1") can be prepared by either

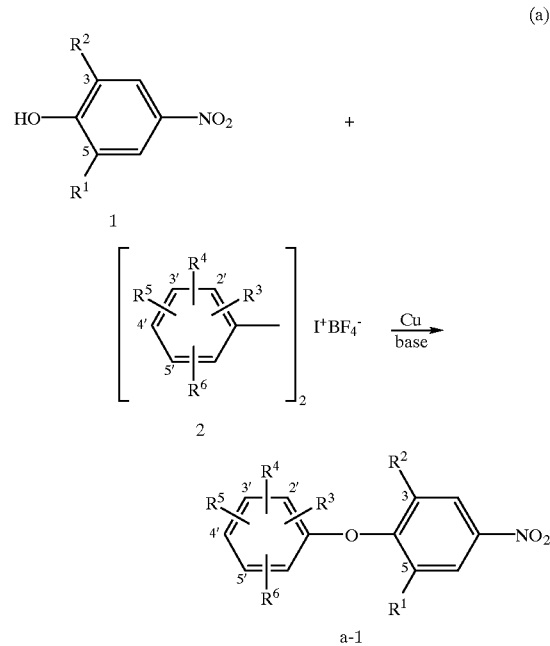

(a)

coupling a 4-nitrophenol (or a corresponding thiophenol) 1 with a bis-aryl iodonium tetrafluoroborate 2 at about RT in a suitable organic solvent such as, for example, dichloromethane, chloroform, DMF or DMSO, in the presence of a suitable copper catalyst such as, for example, copper bronze and a suitable base such as, for example, TEA, potassium-t-butoxide or sodium hydride (*J. Med. Chem,* 38: 695–707 (1995));

(b)

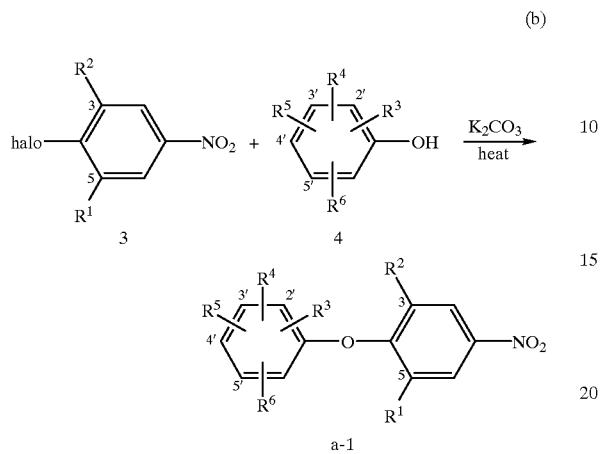

a-1 coupling a 4-halonitrobenzene 3 such as, for example, a 4-iodonitrobenzene, a 4-bromonitrobenzene or a 4-chloronitrobenzene, with a phenol (or a thiophenol) 4 at a suitable elevated temperature (greater than about 120° C.) in the presence of a suitable base such as, for example, potassium carbonate or potassium-t-butoxide, in a polar inert solvent such as, for example, DMSO or N-methylpyrrolidone; or (c)

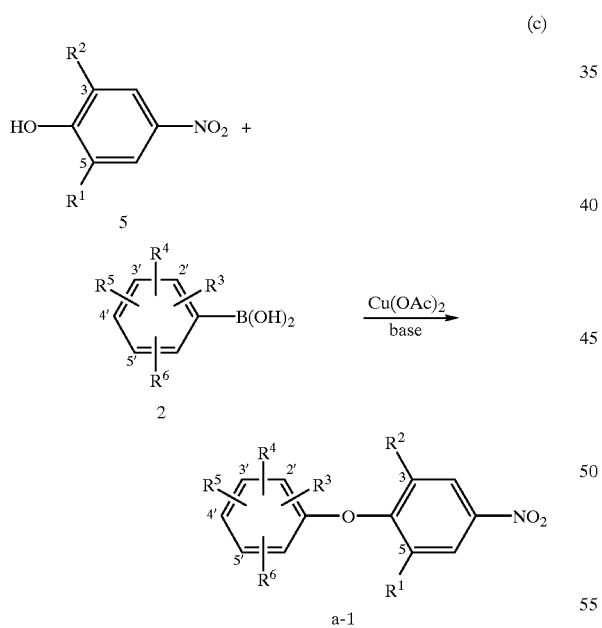

a-1 coupling (at RT in dichloromethane) a phenylboronic acid 2 with a 4-nitrophenol 5 in the presence of copper (II) acetate and a suitable base such as, for example, triethylamine, pyridine or a mixture of triethylamine and pyridine. (*Tetrahedron. Lett.,* 39:2933–2936, 2937–2940 (1998)).

In SCHEME A described hereinbelow, the common intermediate a-2 generated in Step a is the common intermediate a-1 wherein $R^2$ is —CN and $R^5$ is methoxy.

As discussed above, those skilled in the art will understand based upon the present disclosure, e.g., SCHEME A, how to prepare compounds of Formula I of the present invention. For example, those skilled in the art will understand from the present disclosure how to modify SCHEME A, and the details of the Examples described hereinbelow to prepare any specific compound of Formula I of the present invention as desired. It should be understood that SCHEME A is provided solely for the purposes of illustration and does not limit the invention which is defined by the claims.

SCHEME A

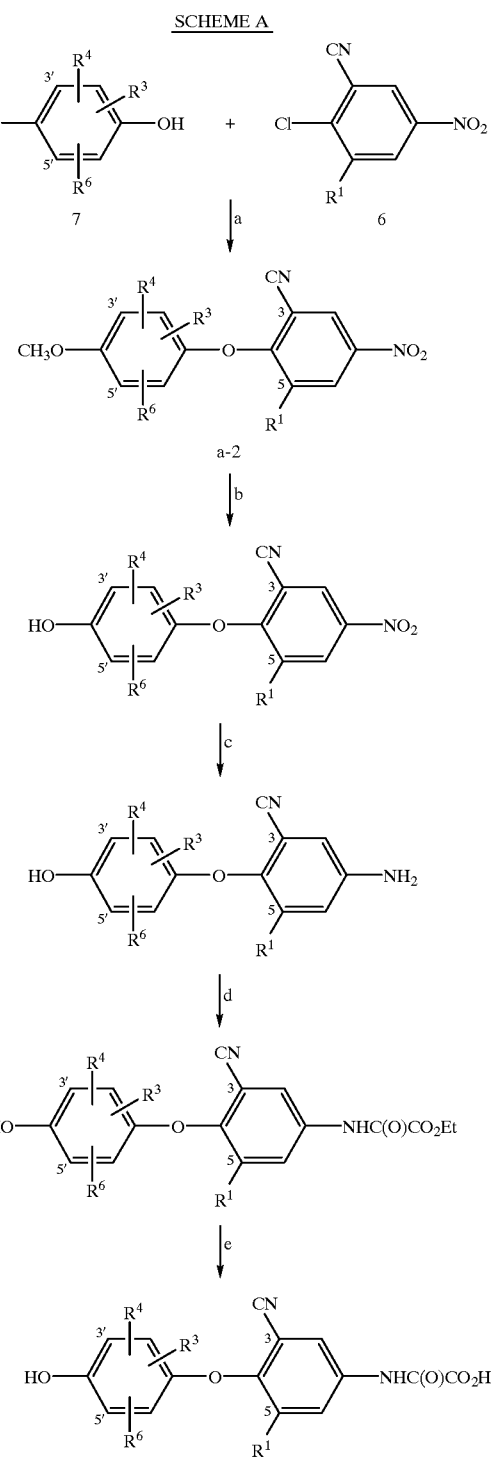

Step a of SCHEME A

As discussed above, the common intermediate a-2 wherein X is oxygen, $R^2$ is —CN, and $R^5$ is methoxy can be prepared by

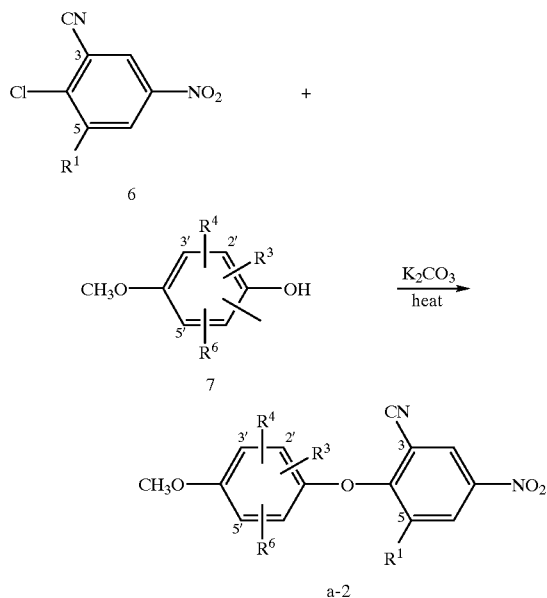

coupling 4-chloronitrobenzene 6 with a phenol 7 at a suitable elevated temperature (greater than about 120° C.) in the presence of a suitable base such as, for example, potassium carbonate or potassium-t-butoxide, in a polar inert solvent such as, for example, DMSO or N-methylpyrrolidone.

Step b of SCHEME A

Demethylation to the phenol can be accomplished by reaction with a suitable boron trihalide such as, for example, boron tribromide or boron trichloride, in a suitable organic solvent such as, for example, dichloromethane or chloroform.

Step c of SCHEME A

Nitro reduction to the aniline can be effected using methods well known in the art such as, for example, hydrogenation or chemical reduction with zinc dust or tin (II) chloride.

Step d of SCHEME A

The aniline can be converted to the oxamate by reaction with diethyl oxalate at elevated temperature (e.g., about 120° C.) for a suitable period of time (e.g., about 5 h), or with ethyl oxalyl chloride at about RT in a suitable anhydrous aprotic solvent such as, for example, DEE, dichloromethane, chloroform or THF.

Step e of SCHEME A

The oxamate may be converted to the oxamic acid using conventional methods well known in the art. For example, the ester may be hydrolyzed to the acid using suitable aqueous alkalides such as, for example, alkali metal carbonates or hydroxides in an aqueous MeOH solution.

In the preparation of the compounds of Formula I it is noted that, as would be appreciated by those skilled in the art, some of the methods useful for the preparation of such compounds may require protection of a particular functionality, e.g., to prevent interference by such functionality in reactions at other sites within the molecule or to preserve the integrity of such functionality. The need for, and type of, such protection is readily determined by one skilled in the art, and will vary depending on, for example, the nature of the functionality and the conditions of the selected preparation method, see, e.g., T. W. Greene, *Protective Groups in Organic Synthesis*, John Wiley & Sons, New York, 1991. Suitable protecting groups for any particular functionality would include those which are not substantially chemically reactive under the reaction conditions described and which can be removed without substantially chemically altering other functionalities of any given intermediate of the compound of Formula I, or of the compound of Formula I itself. The protecting group can be removed as so desired in any given preparation method, e.g., in a subsequent step.

Some of the Formula I compounds of this invention are acidic and they form a salt with a pharmaceutically acceptable cation. Some of the Formula I compounds of this invention are basic and they form a salt with a pharmaceutically acceptable anion. All such salts are within the scope of this invention and they can be prepared by conventional methods such as combining the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, or, in the case of aqueous solutions, by lyophilization, as appropriate. The compounds can be obtained in crystalline form by dissolution in an appropriate solvent(s) such as ethanol, hexanes or water/ethanol mixtures.

Preferred anorectic agents in the compositions, methods and kits of this invention include phenylpropanolamine, ephedrine, pseudoephedrine, phentermine, a neuropeptide Y antagonist, a cholecystokinin-A agonist, a monoamine reuptake inhibitor, a sympathiomimetic agent, a serotoninergic agent, a dopamine agonist, a melanocyte-stimulating hormone receptor agonist or mimetic, a cannabinoid receptor antagonist, a melanocyte-stimulating hormone analog, a melanin concentrating hormone antagonist, the OB protein, a leptin analog, a galanin antagonist and an orexin receptor antagonist.

A preferred monoamine reuptake inhibitor is sibutramine.

Preferred serotoninergic agents include dexfenfluramine and fenfluramine.

A preferred dopamine agonist is bromocriptine.

A preferred lipase inhibitor is tetrahydrolipstatin.

Suitable anorectic agents for the compositions, methods and kits of this invention can be prepared using methods known to those skilled in the art, for example, phentermine can be prepared as described in U.S. Pat. No. 2,408,345; sibutramine can be prepared as described in U.S. Pat. No. 4,929,629; fenfluramine and dexfenfluramine can be prepared as described in U.S. Pat. No. 3,198,834; and bromocriptine can be prepared as described in U.S. Pat. Nos. 3,752,814 and 3,752,888.

Suitable lipase inhibitors can be prepared using methods known to those skilled in the art, for example, tetrahydrolipstatin {(2S,3S,5S)-5-[(S)-2-formamido-4-methylvaleryloxy]-2-hexyl-3-hydroxy-hexadecanoic 1,3 acid lactone} can be prepared as described in, e.g., U.S. Pat. Nos. 5,274,143; 5,420,305; 5,540,917; and 5,643,874.

The administration of a compound, prodrug, isomer or pharmaceutically acceptable salt of the present invention and an anorectic agent or a lipase inhibitor, as the case may be, according to this invention can be sequential in time or simultaneous with the simultaneous method being generally preferred. For sequential administration, a compound, a prodrug, an isomer or a pharmaceutically acceptable salt of the present invention and an anorectic agent or a lipase inhibitor, as the case may be, can be administered in any order. In addition, for sequential administration, the compound, prodrug, isomer or pharmaceutically acceptable salt of the present invention and the anorectic agent (or the lipase inhibitor as the case may be), can be administered in any order. It is generally preferred that such administration be oral. It is even more preferred that the administration be oral and simultaneous. However, for example, if the subject being treated is unable to swallow, or oral absorption is otherwise impaired or undesirable, parenteral or transdermal administration will be appropriate. Where the administration is sequential, the administration of a compound, prodrug, isomer or pharmaceutically acceptable salt of the present invention and an anorectic agent or a lipase inhibitor, as the case may be, can be by the same method or by different methods.

The dose of a compound, prodrug, isomer or pharmaceutically acceptable salt of this invention to be administered to a human or animal is rather widely variable and subject to the judgment of the attending physician or veterinarian. As would be understood by those skilled in the art, it may be necessary to adjust the dose of a compound, prodrug or isomer of this invention when it is administered in the form of a salt, e.g., where the salt forming moiety of which has an appreciable molecular weight. The general range of effective administration rates of the compounds, prodrugs, isomers or pharmaceutically acceptable salts of this invention is from about 0.001 mg/kg body weight to about 100 mg/kg body weight of the subject per day. A preferred range of effective administration rates of the compounds, prodrugs, isomers or pharmaceutically acceptable salts of this invention is from about 0.01 mg/kg body weight to about 50 mg/kg body weight of the subject per day. While it may be practical to administer the daily dose of a compound, prodrug, isomer or pharmaceutically acceptable salt of this invention, in portions, at various hours of the day, in any given case, the amount of compound, prodrug, isomer or pharmaceutically acceptable salt administered will depend on such factors as the solubility of the compound, prodrug, isomer or pharmaceutically acceptable salt of this invention, the formulation used and the route of administration (e.g., orally, transdermally, parenterally or topically).

Dosages of the compounds, prodrugs, isomers and pharmaceutically acceptable salts of the present invention can be administered to humans by any suitable route, with oral administration being preferable. Individual tablets or capsules should generally contain from about 0.1 mg to about 100 mg of compound, prodrug, isomer or pharmaceutically acceptable salt of this invention, in a suitable pharmaceutically acceptable vehicle, diluent or carrier. Dosages for intravenous administration are generally within the range of from about 0.1 mg to about 10 mg per single dose as required. For intranasal or inhaler administration, the dosage is generally formulated as from about a 0.1% to about a 1% (w/v) solution. In practice, the physician will determine the actual dosage which will be most suitable for an individual patient and it will vary with, e.g., age, weight and response of the particular patient. The above dosages are exemplary of the average case but there can, of course, be individual instances where higher or lower dosage ranges are merited, and all such dosages of compounds, prodrugs, isomers and pharmaceutically acceptable salts of this invention, are within the scope of the present invention.

Any suitable dosage of an anorectic agent can be used in aspects of the present invention comprising such agents. The dosage of the anorectic agent is generally in the range of from about 0.01 to about 50 mg/kg body weight of the subject per day, preferably from about 0.1 to about 10 mg/kg body weight of the subject per day, administered singly or as a divided dose. For example, where the anorectic agent is phentermine, the dosage of phentermine is from about 0.01 to 50 mg/kg body weight of the subject per day, preferably from about 0.1 to about 1 mg/kg body weight of the subject per day. In addition, where the anorectic agent is sibutramine, the dosage range is from about 0.01 to about 50 mg/kg body weight of the subject per day, preferably from about 0.1 to about 1 mg/kg body weight of the subject per day; where the anorectic agent is dexfenfluramine or fenfluramine, the dosage range is from about 0.01 to about 50 mg/kg body weight of the subject per day, preferably from about 0.1 to about 1 mg/kg body weight of the subject per day; and where the anorectic agent is bromocriptine, the dosage range is from about 0.01 to about 10 mg/kg body weight of the subject per day, preferably from about 0.1 to about 10 mg/kg body weight of the subject per day. In practice, the physician will determine the actual dosage of anorectic agent which will be most suitable for an individual patient and it will vary with, e.g., age, weight and response of the particular patient. The above dosages of anorectic agents are exemplary but there can, of course, be individual instances where higher or lower dosage ranges of such anorectic agents are merited, and all such dosages are within the scope of the present invention.

Any suitable dosage of a lipase inhibitor can be used in aspects of the present invention comprising such inhibitors. The dosage of the lipase inhibitor is generally in the range of from about 0.01 to about 50 mg/kg body weight of the subject per day, preferably from about 0.05 to about 10 mg/kg body weight of the subject per day, administered singly or as a divided dose. For example, where the lipase inhibitor is tetrahydrolipstatin, the dosage of tetrahydrolipstatin is preferably from about 0.05 to 2 mg/kg body weight of the subject per day. In practice, the physician will determine the actual dosage of lipase inhibitor which will be most suitable for an individual patient and it will vary with, e.g., age, weight and response of the particular patient. The above dosages of lipase inhibitors are exemplary but there can, of course, be individual instances where higher or lower dosage ranges of such lipase inhibitors are merited, and all such dosages are within the scope of the present invention.

Any suitable route of administration may be used in the present invention. It is usually preferred to administer the compounds, prodrugs, isomers and pharmaceutically acceptable salts of this invention orally for reasons of convenience; however, they may be administered, for example, percutaneously, or as suppositories for absorption by the rectum, as desired in a given instance. As described above, the administration may be carried out in single or multiple doses, as appropriate.

The compounds, prodrugs, isomers and pharmaceutically acceptable salts of this invention may be administered alone, and are preferably administered as pharmaceutical compositions comprising a pharmaceutically acceptable vehicle, carrier or diluent. The pharmaceutical compositions of the invention will comprise a suitable amount of a compound, prodrug, isomer or pharmaceutically acceptable salt of this invention, i.e., an amount sufficient to provide the desired dosage.

The compounds, prodrugs, isomers and pharmaceutically acceptable salts of this invention can be administered in a wide variety of different dosage forms, i.e., they may be combined with various pharmaceutically acceptable inert carriers in any suitable form. Such carriers include solid diluents or fillers, sterile aqueous media and various non-toxic organic solvents. The pharmaceutical compositions can be formulated to contain a daily dose, or a convenient fraction of a daily dose, in a dosage unit, which may be a single tablet or a capsule or a convenient volume of a liquid.

All of the usual types of pharmaceutical compositions may be used in the present invention, including tablets, lozenges, hard candies, chewable tablets, granules, powders, sprays, capsules, pills, microcapsules, solutions, parenteral solutions, troches, injections (e.g., intravenous, intraperitoneal, intramuscular or subcutaneous), suppositories, elixirs, syrups and suspensions.

For parenteral administration, the compounds, prodrugs, isomers and pharmaceutically acceptable salts of this invention may be used as solutions in sesame or peanut oil, or as aqueous solutions (e.g., aqueous propyleneglycol), as the case may be, and they are best used in the form of a sterile aqueous solution which may contain other substances; for example, enough salts or glucose to make the solution isotonic, the pH of the solution being suitably adjusted and buffered, where necessary, and surfactants such as, for example, hydroxypropylcellulose. Such oily solutions are suitable for intra-articular, intramuscular and subcutaneous injection purposes. Such aqueous solutions are suitable for intravenous injection purposes.

The compounds of this invention may also be administered topically and this may be done by way of, e.g., creams, jellies, salves, lotions, gels, pastes, ointments, and the like, in accordance with standard pharmaceutical practice. The compounds of the present invention may also be administered transdermally (e.g., through the use of a patch).

Any suitable formulation for transdermal application comprising a compound of the present invention may be employed and such formulations would generally also contain a suitable transdermal carrier, e.g., an absorbable pharmacologically acceptable solvent to promote and assist passage of the compounds through the subject's skin. For example, suitable transdermal devices may comprise the form of a bandage having a backing member and a reservoir containing the subject compound. Such bandage-type transdermal devices may further include suitable carriers, rate-controlling barriers, and means for securing the transdermal device to the subject's skin.

As will be described in detail hereinbelow, the pharmaceutical compositions can be prepared by methods commonly employed using conventional, organic or inorganic additives, such as an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylpyrrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate, or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g., sodium benzoate, sodium bisulfite, methylparaben or propylparaben), a stabilizer (e.g., citric acid, sodium citrate or acetic acid), a suspending agent (e.g., methylcellulose, polyvinylpyrrolidone, or aluminum stearate), a dispersing agent (e.g., hydroxypropylmethylcellulose), a diluent (e.g., water), a coloring agent, an emulsifying agent, and a base wax (e.g., cocoa butter, white petrolatum or polyethylene glycol).

Any of the compounds, prodrugs, isomers or pharmaceutically acceptable salts of this invention may be readily formulated as tablets, capsules, and the like. It is preferable to prepare solutions from water-soluble salts, such as the hydrochloride salt.

In general, all of the pharmaceutical compositions are prepared according to methods usual in pharmaceutical chemistry.

Capsules can be prepared by mixing a compound, prodrug, isomer or pharmaceutically acceptable salt of the invention with a suitable diluent and filling the proper amount of the mixture in capsules. The usual diluents include inert powdered substances such as starch of many different kinds, powdered cellulose, especially crystalline and microcrystalline cellulose, sugars such as fructose, mannitol and sucrose, grain flours and similar edible powders.

Tablets can be prepared by direct compression, by wet granulation, or by dry granulation. Their formulations usually incorporate diluents, binders, lubricants and disintegrators as well as a compound, prodrug, isomer or pharmaceutically acceptable salt of this invention. Common diluents include, for example, various types of starch, lactose, mannitol, kaolin, calcium phosphate or sulfate, inorganic salts such as sodium chloride and powdered sugar. Powdered cellulose derivatives may also be used. Common tablet binders include substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant is generally necessary in a tablet formulation to prevent the tablet and punches from sticking in the die. The lubricant is chosen from such slippery solids as talc, magnesium and calcium stearate, stearic acid and hydrogenated vegetable oils.

Tablet disintegrators include substances which swell when wetted to break up the tablet and release a compound, prodrug, isomer or pharmaceutically acceptable salt of this invention. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethylcellulose, for example, may be used as well as sodium lauryl sulfate.

Tablets are often coated with sugar as a flavor and sealant, or with film-forming protecting agents to modify the dissolution properties of the tablet. The compounds of the invention may also be formulated as chewable tablets, by using large amounts of pleasant-tasting substances such as mannitol in the formulation, as is now well-established in the art.

Where it is desired to administer a compound, prodrug, isomer or pharmaceutically acceptable salt of this invention as a suppository, any suitable base can be used. Cocoa butter is a traditional suppository base, which may be modified by the addition of waxes to raise its melting point. Water-miscible suppository bases comprising, particularly, polyethylene glycols of various molecular weights are in wide use.

As discussed above, the effect of a compound, prodrug, isomer or pharmaceutically acceptable salt of this invention may be delayed or prolonged by proper formulation. For example, a slowly soluble pellet of a compound, prodrug, isomer or pharmaceutically acceptable salt of this invention may be prepared and incorporated in a tablet or capsule. The technique may be improved by making pellets of several different dissolution rates and filling capsules with a mixture of the pellets. Tablets or capsules may be coated with a film which resists dissolution for a predictable period of time. The parenteral preparations may also be made long-acting by dissolving or suspending a compound, prodrug, isomer or pharmaceutically acceptable salt of this invention, as the case may be, in oily or emulsified vehicles which allow it to disperse only slowly in the serum.

The compounds, prodrugs, isomers and pharmaceutically acceptable salts of this invention may also be administered to a mammal other than a human. The method of administration and the dosage to be administered to such a mammal will depend, for example, on the animal species and the disease or disorder being treated. The compounds, prodrugs, isomers and pharmaceutically acceptable salts of this invention may be administered to animals in any suitable manner, e.g., orally, parenterally or transdermally, in any suitable form such as, for example, a capsule, bolus, tablet, pellet, e.g., prepared by admixing a compound, prodrug, isomer or pharmaceutically acceptable salt of this invention with a suitable diluent such as carbowax or carnuba wax together with a lubricant, liquid drench or paste, e.g., prepared by dispersing a compound, prodrug, isomer or pharmaceutically acceptable salt of this invention in a pharmaceutically acceptable oil such as peanut oil, sesame oil or corn oil. The compounds, prodrugs, isomers or pharmaceutically acceptable salts of this invention may also be administered to animals as an implant. Such formulations are prepared in a conventional manner in accordance with standard veterinary practice. As an alternative, the compounds, prodrugs, isomers and pharmaceutically acceptable salts of this invention may be administered with the water supply, e.g., in the form of a liquid or water-soluble concentrate. In addition, the compounds, prodrugs, isomers and pharmaceutically acceptable salts of this invention, e.g., within the pharmaceutical compositions of the invention, may be administered in the animal feedstuff, e.g., a concentrated feed additive or premix may be prepared for mixing with the normal animal feed, commonly along with a suitable carrier therefor. The carrier facilitates uniform distribution of the compound, prodrug, isomer or pharmaceutically acceptable salt of this invention in the, e.g., finished feed with which the premix is blended. Suitable carriers include, but are not limited to, liquids, e.g., water, oils such as soybean, corn, cottonseed, or volatile organic solvents, and solids, e.g., a small portion of the feed or various suitable meals including alfalfa, soybean, cottonseed oil, linseed oil, corncob, corn, molasses, urea and bone, and mineral mixes.

Since the present invention has an aspect that relates to the treatment of the disease/conditions described herein with a combination of active ingredients which may be administered separately, the invention also relates to combining separate pharmaceutical compositions in kit form. The kit comprises two separate pharmaceutical compositions: a compound of Formula I, or a prodrug thereof, or a geometric or optical isomer thereof, or a pharmaceutically acceptable salt of such compound, prodrug, or isomer, and a second compound as described above. The kit comprises a container for containing the separate compositions such as a divided bottle or a divided foil packet. Typically the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. Second Week, Monday, Tuesday, . . . " etc. Other variations of memory aids will be readily apparent. A "daily dose" can be a single tablet or capsule or several tablets or capsules to be taken on a given day. Also, a daily dose of a compound of Formula I, or a prodrug thereof, or a geometric or optical isomer thereof, or a pharmaceutically acceptable salt of such compound, prodrug or isomer, can consist of one tablet or capsule while a daily dose of the second compound can consist of several tablets or capsules and vice versa. The memory aid should reflect this.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

Utility of the compounds of Formula I, or the isomers thereof, or the pharmaceutically acceptable salts of such compounds, or isomers thereof, can be evidenced by activity in at least one of the two assays described below.

Assay 1

Oxygen Consumption

As would be appreciated by those skilled in the relevant art, during increased energy expenditure, animals generally consume more oxygen. In addition, metabolic fuels such as, for example, glucose and fatty acids, are oxidized to $CO_2$ and $H_2O$ with the concomitant evolution of heat, commonly referred to in the art as thermogenesis. Thus, the measurement of oxygen consumption in animals, including humans and companion animals, is an indirect measure of thermogenesis. Indirect calorimetry is commonly used in animals, e.g., humans, by those skilled in the relevant art to measure such energy expenditures.

Those skilled in the art understand that increased energy expenditure and the concomitant burning of metabolic fuels resulting in the production of heat may be efficacious with respect to the treatment of, e.g., obesity. As is well known by those skilled in the art, thyroid hormones affect cardiac functioning, for example, by causing an increase in the heart rate and, accordingly, an increase in oxygen consumption with concomitant heat production.

The ability of the compounds, isomers thereof, and pharmaceutically acceptable salts of said compounds and isomers of this invention to generate a thermogenic response may be demonstrated according to the following protocol.

A. Experimental

This in vivo screen is designed to evaluate the efficacy and cardiac effects of compounds that are tissue-selective thyroid hormone agonists. The efficacy endpoints measured are whole body oxygen consumption and the activity of liver mitochondrial alpha-glycerophosphate dehydrogenase ("mGPDH"). The cardiac endpoints that are measured are heart weight and heart mGPDH activity. The protocol involves: (a) dosing fatty Zucker rats for about 6 days, (b) measuring oxygen consumption and (c) harvesting tissue for preparation of mitochondria and subsequent assaying of enzyme activity thereby.

B. Preparation of Rats

Male fatty Zucker rats having a body weight range of from about 400 g to about 500 g are housed for from about 3 to about 7 days in individual cages under standard laboratory conditions prior to the initiation of the study.

A compound of Formula I, or an isomer thereof, or a pharmaceutically acceptable salt of such compound or isomer, vehicle or $T_3$ sodium salt, is administered by oral gavage as a single daily dose given between about 3 p.m. to about 6 p.m. for about 6 days. A compound of Formula I, or an isomer thereof, or a pharmaceutically acceptable salt of such compound or isomer, or $T_3$ sodium salt is dissolved in a suitably small volume of about 1N NaOH and then brought up to a suitable volume with about 0.01N NaOH containing about 0.25% of methyl cellulose (10:1, 0.01N NaOH/MC:1N NaOH). The dosing volume is about 1 ml.

C. Oxygen Consumption

About 1 day after the last dose of the compound is administered, oxygen consumption is measured using an open circuit, indirect calorimeter (Oxymax, Columbus Instruments, Columbus, Ohio 43204). The Oxymax gas sensors are calibrated with $N_2$ gas and a gas mixture (about 0.5% of $CO_2$, about 20.5% of $O_2$, about 79% of $N_2$) before each experiment.

The subject rats are removed from their home cages and their body weights recorded. The rats are placed into the sealed chambers (43×43×10 cm) of the Oxymax, the chambers are placed in the activity monitors, and the air flow rate through the chambers is then set at from about 1.6 L/min to about 1.7 L/min.

The Oxymax software then calculates the oxygen consumption (mL/kg/h) by the rats based on the flow rate of air through the chambers and the difference in oxygen content at the inlet and output ports. The activity monitors have 15 infrared light beams spaced about one inch apart on each axis, and ambulatory activity is recorded when two consecutive beams are broken, and the results are recorded as counts.

Oxygen consumption and ambulatory activity are measured about every 10 min for from about 5 h to about 6.5 h. Resting oxygen consumption is calculated on individual rats by averaging the values excluding the first 5 values and the values obtained during time periods where ambulatory activity exceeds about 100 counts.

Assay 2

Binding to Thyroid Hormone Receptors

The ability of a compound of Formula I, or an isomer thereof, or a pharmaceutically acceptable salt of such compound or isomer, ("the test thyromimetic compounds"), to bind to thyroid hormone receptors can be demonstrated in the following protocol.

A. Preparation of Insect Cell Nuclear Extracts

High Five cell pellets (BTI-TN-5B1-4, catalogue number B855-02, Invitrogen®, Carlsbad, Calif.) obtained about 48 h after infection with baculovirus (GibcoBRL®, Gaithersburg, Md.) expressing either human TRα or TRβ were suspended in ice cold Sample Buffer (10 mM Tris, pH 8.0; 1 mM $MgCl_2$; 1 mM DTT; 0.05% Tween 20; 1 mM 4-(2-aminoethyl)-benzenesulfonylfluoride; 25 µg/mL leupeptin). After about 10 min incubation on ice, the suspension was homogenized by 20 strokes with a Dounce homogenizer (VWR® Scientific Products, West Chester, Pa.) and centrifuged at 800×g for about 15 min at 4° C. The pellet (nuclei) was suspended in a hypertonic buffer (0.4 M KCl; 10 mM Tris, pH 8.0; 1 mM $MgCl_2$; 1 mM DTT; 0.05% Tween 20) and incubated for about 30 min on ice. The suspension was centrifuged at 100,000×g for about 30 min at 4° C. The supernatant (nuclear extract) was stored in 0.5 mL aliquots at −80° C.

B. Binding Assay

Competition binding assays to measure the interaction of the test thyromimetic compounds with thyroid hormone receptor α1 and β1 (TRα and TRβ) are carried out according to the following protocol.

Solutions of test thyromimetic compounds (final compound concentration of 20 mM) are prepared using 100% DMSO as a solvent. Each compound is serially diluted in an assay buffer (5 mM Tris-HCl, pH 8.0; 50 mM NaCl; 2 mM EDTA; 10% (v/v) glycerol; 1 mM DTT, "assay buffer") containing 0.4 nM $^{125}$I-$T_3$ (specific activity of about 220 Ci/mmol) to yield solutions that varied in compound concentration from about 10 µM to about 0.1 nM.

High Five insect cell nuclear extract containing either TRα or TRβ is diluted to a total protein concentration of 0.0075 mg/mL using the assay buffer as diluent.

One volume (100 µL) of each thyromimetic compound dilution (containing 0.4 nM $^{125}$I-T3) is combined with an equal volume (100 µL) of diluted nuclear extract containing TRα1 or TRβ1, and incubated at RT for about 90 min. 150 µL sample of the binding reaction is removed and placed into a 96-well filter plate (Millipore®, Bedford, Mass.) that had been pre-washed with ice-cold assay buffer. The plate is subjected to vacuum filtration using a filtration manifold (Millipore®). Each well is washed five times by the addition of 200 µL of ice-cold assay buffer and subsequent vacuum filtration. The plate is removed from the vacuum filtration manifold, the bottom of the plate is briefly dried on paper towels, then 25 µL of Wallac® (EG&G Wallac®, Gaithersburg, Md.) Optiphase Supermix scintillation cocktail is added to each well and the top of the plate is covered with plastic sealing tape (Microplate Press-on Adhesive Sealing Film, Packard® Instrument Co., Inc., Downers Grove, Ill.) and the radioactivity is quantitated using a Wallac® Microbeta 96-Well plate scintillation counter.

The following EXAMPLES are provided solely for the purposes of illustration and do not limit the invention which is defined by the claims.

EXAMPLE 1

2-Cyano-6-methylphenol

A solution of 2-hydroxy-3-methylbenzaldehyde (18.6 g), hydroxylamine hydrochloride (14.2 g) and sodium formate (19.2 g) in formic acid (200 mL) was heated at reflux for 18 h, then cooled and partitioned between DEE/water. The organic layer was washed with water, saturated aqueous sodium bicarbonate and brine, then dried over sodium sulfate and concentrated in vacuo to afford a solid. Recrystallization from diethyl ether/petroleum ether afforded the title compound as colorless crystals (15.0 g).

EXAMPLE 2

3-Cyano-4-hydroxy-5-methylnitrobenzene

To a heated (45° C.), stirred solution of 2-cyano-6-methylphenol (5 g) in glacial acetic acid (32 mL) was added a solution of fuming nitric acid (3.2 mL) in acetic acid (12 mL). After 1 h at elevated temperature (45° C.), the reaction mixture was cooled (to 0° C.), water added and partitioned between DEE/water. The organic phase was washed with water, brine, dried over sodium sulfate and concentrated in vacuo to afford a solid. Recrystallization from DEE afforded the title compound as yellow crystals (3.6 g).

EXAMPLE 3

3-isopropyl-4-methoxybromobenzene

A solution of 2-methoxyisopropyl-benzene (2 g) and N-bromosuccinimide (2.6 g) in acetonitrile (20 mL) was stirred at ambient temperature for 18 h. The reaction was concentrated in vacuo, slurried in carbon tetrachloride and filtered. The filtrate was concentrated in vacuo. The residue was flash chromatographed (5% dichloromethane/hexanes) to afford the title compound as an oil (2.5 g).

EXAMPLE 4

3-Isopropyl-4-methoxybenzene boronic acid

To a cooled (−78° C.), stirred solution of 3-isopropyl-4-methoxybromobenzene (2.5 g) was added n-butyllithium (4.8 mL of a 2.5 M solution in hexanes) dropwise. After 30 min, triisopropylborate (5 mL) was added and the reaction solution was allowed to warm to RT and then stirred for 18 h. The reaction solution was concentrated in vacuo, saturated aqueous sodium bicarbonate was added and the resulting mixture was stirred for 30 min. The reaction was extracted with ethyl acetate. The organic layer was washed with water then brine, dried over sodium sulfate, and concentrated in vacuo to afford a solid, which was triturated with hexanes to afford the title compound as colorless plates (1.1 g).

EXAMPLE 5

4-Methoxy-5,6,7,8-tetrahydronaphthalen-1-ol

To a cooled (0° C.), stirred solution of 5-hydroxy-8-methoxy-3,4-dihydro-2H-naphthalen-1-one (1.7 g) in trifluoroacetic acid (20 mL) triethylsilane (4.2 mL) was added and the reaction warmed to RT and then stirred for 1.5 h). The reaction mixture was concentrated in vacuo, partitioned between ethyl acetate/water, the organic layer was washed with water, brine, and then dried over sodium sulfate and concentrated in vacuo. The resulting oil is flash chromatographed (10% ethyl acetate/hexanes) to afford the title compound as a colorless solid (1.6 g).

EXAMPLE 6

N-[3-Cyano-4-(4-hydroxy-3-isopropyl-phenoxy)-5-methyl-phenyl]-oxamic acid ethyl ester

Step A

A mixture of 3-isopropyl-4-methoxyphenol (200 mg), 4-chloro-3-cyano-5-methylnitrobenzene (200 mg) and potassium carbonate (211 mg) in methylethylketone (8 mL) was refluxed for 18 h. The dark mixture was concentrated in vacuo, partitioned between ethyl acetate/water, the organic layer washed with about 2N sodium hydroxide, brine, dried over sodium sulfate and concentrated to a dark oil. Flash chromatography (10% ethyl acetate/hexanes) afforded 2-(3-isopropyl-4-methoxy-phenoxy)-3-methyl-5-nitrobenzonitrile as a yellow oil (300 mg).

Step B

To a cooled (−78° C.), stirred solution of 2-(3-isopropyl-4-methoxy-phenoxy)-3-methyl-5-nitrobenzonitrile (308 mg) in dichloromethane (5 mL) was added boron tribromide (0.31 mL) dropwise. The reaction was allowed to warm to RT and stirred for 1 h, quenched with water and stirred for 20 min. The reaction was extracted with ethyl acetate, the organic phase washed with water, saturated aqueous brine, dried over sodium sulfate and concentrated in vacuo. Flash chromatography (20% ethyl acetate/hexanes) on silica gel afforded 2-(3-isopropyl-4-hydroxy-phenoxy)-3-methyl-5-nitrobenzonitrile as a yellow oil (215 mg).

Step C

A solution of 2-(3-isopropyl-4-hydroxy-phenoxy)-3-methyl-5-nitrobenzonitrile (215 mg) and stannous chloride (776 mg) in ethanol (5 mL) was refluxed for 2 h, cooled, quenched with saturated aqueous sodium bicarbonate and concentrated in vacuo. The residue was extracted with ethyl acetate, the organics washed with brine, dried over sodium sulfate and concentrated in vacuo. The residue was flash chromatographed (40% ethyl acetate/hexanes) to afford 5-amino-2-(3-isopropyl-4-hydroxy-phenoxy)-3-methyl-benzonitrile as a colorless foam (150 mg).

Step D

A solution of 5-amino-2-(3-isopropyl-4hydroxy-phenoxy)-3-methylbenzonitrile (150 mg) in diethyl oxylate (0.7 mL) was heated at 130° C. for 18 h. Flash chromatography (40% ethyl acetate/hexanes) of the reaction solution afforded N-[3-cyano-4-(4-hydroxy-3-isopropyl-phenoxy)-5-methyl-phenyl]-oxamic acid ethyl ester as a colorless solid (118 mg). MS Found: 381.

EXAMPLE 7

N-[3-Cyano-4-(4-hydroxy-3-isopropyl-phenoxy)-5-methyl-phenyl]-oxamic acid

Step A

Step A of EXAMPLE 6.

Step B

Step B of EXAMPLE 6.

Step C

Step C of EXAMPLE 6.

Step D

Step D of EXAMPLE 6.

Step E

A solution of N-[3-cyano-4-(4-hydroxy-3-isopropyl-phenoxy)-5-methyl-phenyl]-oxamic acid ethyl ester (110 mg) and 1N aqueous sodium hydroxide (0.6 mL) in EtOH (1 mL) was stirred at ambient temperature for 10 min, partitioned between ethyl acetate/1N aqueous hydrochloric acid, the organic layer washed with brine, dried over sodium sulfate and concentrated in vacuo to afford the title compound as a colorless solid (9 mg). MS: 353.

Using the appropriate starting materials, the compound, N[3-chloro-5-cyano-4-(4-hydroxy-3-isopropyl-phenoxy)-phenyl]-oxamic acid, was prepared in an analogous manner to the sequence of reactions described for EXAMPLE 7. MS Found: 373.

What is claimed is:
1. A compound of the Formula

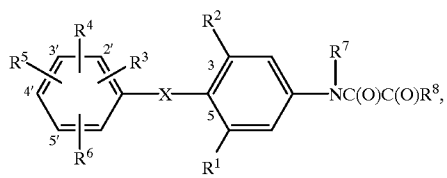

(I)

a prodrug thereof, a geometric or optical isomer thereof, or a pharmaceutically acceptable salt of said compound, said prodrug, or said isomer, wherein:

$R^1$ and $R^2$ are independently halogen, $C_{1-8}$ alkyl, —CN or $C_{1-8}$ perfluoroalkyl; provided that at least one of $R^1$ and $R^2$ is —CN;

$R^3$ is hydrogen or $C_{1-8}$ alkyl;

$R^4$ is halogen, $C_{1-8}$ perfluoroalkyl, $C_{1-8}$ alkyl, $C_{1-8}$ alkanoyl, hydroxy-($C_{1-8}$ alkyl), aryl optionally substituted with Y and Z, aryl-($C_{1-8}$ alkyl), carbocyclic aroyl optionally substituted with Y and Z, $C_{3-10}$ cycloalkyl optionally substituted with Y and Z, or $C_{3-10}$ cycloalkyl-($C_{1-8}$ alkyl);

or $R^4$ is the radical

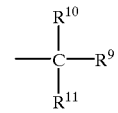

wherein: $R^9$ is hydrogen, $C_{1-8}$ alkyl, aryl optionally substituted with Y and Z, aryl-($C_{1-8}$ alkyl), $C_{3-10}$ cycloalkyl optionally substituted with Y and Z, or ($C_{3-10}$ cycloalkyl-($C_{1-8}$ alkyl); $R^{10}$ is —$OR^{14}$; $R^{11}$ is hydrogen or $C_{1-8}$ alkyl; or $R^{10}$ and $R^{11}$ may be taken together with the carbon atom to which they are attached to form a carbonyl group;

$R^5$ is hydroxy, esterified hydroxy or etherified hydroxy;

$R^6$ is hydrogen, halogen, $C_{1-8}$ alkyl or $C_{1-8}$ perfluoroalkyl;

$R^7$ is hydrogen, $C_{1-8}$ alkyl or $C_{1-8}$ perfluoroalkyl;

$R^8$ is —$OR^{12}$ or —$NR^{12}R^{13}$;

$R^{12}$ and $R^{13}$ are each independently hydrogen or $C_{1-8}$ alkyl;

$R^{14}$ is hydrogen, $C_{1-8}$ alkyl or $C_{1-8}$ acyl;

X is O, $S(O)_a$, C=O or $NR^{15}$;

a is 0, 1 or 2;

$R^{15}$ is hydrogen or $C_{1-8}$ alkyl;

Y and Z for each occurrence are independently (a) hydrogen, (b) halogen, (c) trifluoromethyl, (d) —$OCF_3$, (e) —CN, (f) $C_{1-6}$ alkyl optionally substituted with one or more substituents independently selected from the group consisting of halogen, —$OCF_3$, —$CF_3$ and phenyl, (g) $C_{1-6}$ alkoxy, (h) aryl optionally substituted with one or more substituents independently selected from the group consisting of halogen, —$OCF_3$, —$CF_3$, $C_{1-4}$ alkyl and $C_{1-4}$ alkoxy, (i) —$C(O)_2R^{16}$, (j) —$C(O)NR^{16}R^{17}$, (k) —$C(O)R^{16}$, (l) —$NR^{16}C(O)NR^{16}R^{17}$ or (m) —$NR^{16}C(O)R^{17}$; or Y and Z for any occurrence may be taken together to form (a) a carbocycle of the formula —$(CH_2)_b$—, or (b) a heterocycle selected from the group consisting of —$O(CH_2)_cO$—, $(CH_2)_dNH$— and —CH=CHNH—;

b is 3, 4, 5, 6 or 7;

c and d are each independently 2, 3, 4, 5 or 6;

$R^{16}$ and $R^{17}$ for each occurrence are independently hydrogen, $C_{1-6}$ alkyl, $C_{2-6}$ alkenyl, —($C_{1-6}$ alkyl)-$C_{1-6}$ alkoxy, aryl optionally substituted with Y and Z, het optionally substituted with Y and Z, —($C_{1-4}$ alkyl)-aryl optionally substituted with Y and Z, —($C_{1-4}$ alkyl)-heterocycle optionally substituted with Y and Z, —($C_{1-4}$ alkyl)-hydroxy, —($C_{1-4}$ alkyl)-halo, —($C_{1-4}$ alkyl)-poly-halo, —($C_{1-4}$ alkyl)-$CONR^{18}R^{19}$ or $C_{3-10}$ cycloalkyl;

het for each occurrence is a heterocyclic ring selected from the group consisting of 4-, 5-, 6-, 7- and 8-membered partially and fully saturated, and unsaturated, heterocyclic rings containing from one to four heteroatoms independently selected from the group consisting of N, O and S, and including any bicyclic group in which said heterocyclic ring is fused to a benzene ring or a heterocyclic ring selected from the group consisting of 4-, 5-, 6-, 7- and 8-membered partially and fully saturated, and unsaturated, heterocyclic rings containing from one to four heteroatoms independently selected from the group consisting of N, O and S; and $R^{18}$ and $R^{19}$ for each occurrence are independently hydrogen, $C_{1-6}$ alkyl, $C_{3-10}$ cycloalkyl or aryl optionally substituted with Y and Z.

2. A compound or pharmaceutically acceptable salt as defined in claim 1 wherein X is oxygen.

3. A compound or pharmaceutically acceptable salt as defined in claim 2 wherein $R^3$ is located at the 2' position, $R^4$ is located at the 3' position, $R^5$ is located at the 4' position, and $R^6$ is located at the 5' position.

4. A compound or pharmaceutically acceptable salt as defined in claim 3 wherein $R^3$, $R^6$ and $R^7$ are hydrogen, and $R^5$ is hydroxy.

5. A compound or pharmaceutically acceptable salt as defined in claim 4 wherein $R^1$ and $R^2$ are each independently —CN, methyl or chloro.

6. A compound or pharmaceutically acceptable salt as defined in claim 5 wherein $R^8$ is —$OR^{12}$.

7. A compound or pharmaceutically acceptable salt as defined in claim 6 wherein $R^{12}$ is hydrogen, methyl or ethyl, and $R^4$ is —$CH(CH_3)_2$.

8. A compound or pharmaceutically acceptable salt as defined in claim 5 wherein $R^8$ is —$NR^{12}R^{13}$.

9. A pharmaceutically acceptable salt as defined in claim 1 wherein said salt is a potassium or sodium salt.

10. A compound, prodrug, isomer or pharmaceutically acceptable salt as defined in claim 1 wherein said compound is N-[3-cyano-4-(4-hydroxy-3-isopropyl-phenoxy)-5-methyl-phenyl]-oxamic acid or N-[3-chloro-5-cyano-4-(4-hydroxy-3-isopropyl-phenoxy)-phenyl]-oxamic acid.

11. A compound, prodrug, isomer or pharmaceutically acceptable salt as defined in claim 10 wherein said compound is N-[3-cyano-4-(4-hydroxy-3-isopropyl-phenoxy)-5-methyl-phenyl]-oxamic acid.

12. A pharmaceutically acceptable salt of N-[3-cyano-4-(4-hydroxy-3-isopropyl-phenoxy)-5-methyl-phenyl]-oxamic acid as defined in claim 11 wherein said salt is a potassium salt.

13. A pharmaceutically acceptable salt of N-[3-cyano-4-(4-hydroxy-3-isopropyl-phenoxy)-5-methyl-phenyl]-oxamic acid as defined in claim 11 wherein said salt is a sodium salt.

14. A compound, prodrug, isomer or pharmaceutically acceptable salt as defined in claim 10 wherein said compound is N-[3-chloro-5-cyano-4-(4-hydroxy-3-isopropyl-phenoxy)-phenyl]-oxamic acid.

15. A pharmaceutically acceptable salt of N-[3-chloro-5-cyano-4-(4-hydroxy-3-isopropyl-phenoxy)-phenyl]-oxamic acid as defined in claim 14 wherein said salt is a potassium salt.

16. A pharmaceutically acceptable salt of N-[3-chloro-5-cyano-4-(4-hydroxy-3-isopropyl-phenoxy)-phenyl]-oxamic acid as defined in claim 14 wherein said salt is a sodium salt.

17. A method of treating a condition selected from the group consisting of obesity, hyperlipidemia, thyroid disease, hypothyroidism, diabetes mellitus, atherosclerosis, hypertension, coronary heart disease, hypercholesteremia, depression and osteoporosis, in a mammal which comprises administering to said mammal an effective treating amount of a compound, prodrug, isomer or pharmaceutically acceptable salt as defined in claim 1.

18. A method as defined in claim 17 wherein said condition is obesity.

19. A method as defined in claim 17 further including administering an anorectic agent.

20. A method as defined in claim 18 further including administering an anorectic agent.

21. A method as defined in claim 19 wherein said anorectic agent is selected from the group consisting of phenylpropanolamine, ephedrine, pseudoephedrine, phentermine, a neuropeptide Y antagonist, a cholecystokinin-A agonist, a monoamine reuptake inhibitor, a sympathiomimetic agent, a serotoninergic agent, a dopamine agonist, a melanocyte-stimulating hormone receptor agonist or mimetic, a cannabinoid receptor antagonist, a melanocyte-stimulating hormone analog, a melanin concentrating hormone antagonist, the OB protein, a leptin analog, a galanin antagonist and an orexin receptor antagonist.

22. A method as defined in claim 21 wherein said anorectic agent is phentermine.

23. A method as defined in claim 21 wherein said monoamine reuptake inhibitor is sibutramine, said serotoninergic agent is dexfenfluramine or fenfluramine, and said dopamine agonist is bromocriptine.

24. A method as defined in claim 17 further including administering a lipase inhibitor.

25. A method as defined in claim 18 further including administering a lipase inhibitor.

26. A method as defined in claim 25 wherein said lipase inhibitor is tetrahydrolipstatin.

27. A pharmaceutical composition comprising a compound, prodrug, isomer or pharmaceutically acceptable salt as defined in claim 1, and a pharmaceutically acceptable vehicle, diluent or carrier.

28. A pharmaceutical composition as defined in claim 27 further comprising an anorectic agent.

29. A pharmaceutical composition as defined in claim 27 further comprising a lipase inhibitor.

30. A pharmaceutical composition for treating a condition selected from the group consisting of obesity, hyperlipidemia, thyroid disease, hypothyroidism, diabetes mellitus, atherosclerosis, hypertension, coronary heart disease, hypercholesteremia, depression and osteoporosis, in a mammal comprising a compound, prodrug, isomer or pharmaceutically acceptable salt as defined in claim 1, and a pharmaceutically acceptable vehicle, diluent or carrier.

31. A pharmaceutical composition as defined in claim 30 wherein said condition is obesity.

32. A pharmaceutical composition as defined in claim 30 further including an anorectic agent.

33. A pharmaceutical composition as defined in claim 31 further including an anorectic agent.

34. A pharmaceutical composition as defined in claim 33 wherein said anorectic agent is selected from the group consisting of phenylpropanolamine, ephedrine, pseudoephedrine, phentermine, a neuropeptide Y antagonist, a cholecystokinin-A agonist, a monoamine reuptake inhibitor, a sympathiomimetic agent, a serotoninergic agent, a dopamine agonist, a melanocyte-stimulating hormone receptor agonist or mimetic, a cannabinoid receptor antagonist, a melanocyte-stimulating hormone analog, a melanin concentrating hormone antagonist, the OB protein, a leptin analog, a galanin antagonist and an orexin receptor antagonist.

35. A pharmaceutical composition as defined in claim 34 wherein said anorectic agent is phentermine.

36. A pharmaceutical composition as defined in claim 34 wherein said monoamine reuptake inhibitor is sibutramine, said serotoninergic agent is dexfenfluramine or fenfluramine, and said dopamine agonist is bromocriptine.

37. A pharmaceutical composition as defined in claim 30 further including a lipase inhibitor.

38. A pharmaceutical composition as defined in claim 31 further including a lipase inhibitor.

39. A pharmaceutical composition as defined in claim 38 wherein said lipase inhibitor is tetrahydrolipstatin.

40. A kit for the treatment of a condition selected from the group consisting of obesity, hyperlipidemia, thyroid disease, hypothyroidism, diabetes mellitus, atherosclerosis, hypertension, coronary heart disease, hypercholesteremia, depression and osteoporosis which comprises: a first compound, said first compound being a compound, prodrug, isomer, or pharmaceutically acceptable salt as defined in claim 1, and a pharmaceutically acceptable vehicle, carrier or diluent, in a first unit dosage form; a second compound, said second compound being an anorectic agent or a lipase inhibitor, and a pharmaceutically acceptable vehicle, carrier or diluent, in a second unit dosage form; and a container.

41. A kit as defined in claim 40 wherein said condition is obesity.

42. A kit as defined in claim 41 wherein said anorectic agent is selected from the group consisting of phenylpropanolamine, ephedrine, pseudoephedrine, phentermine, a neuropeptide Y antagonist, a cholecystokinin-A agonist, a monoamine reuptake inhibitor, a sympathiomimetic agent, a serotoninergic agent, a dopamine agonist, a melanocyte-stimulating hormone receptor agonist or mimetic, a cannabinoid receptor antagonist, a melanocyte-stimulating hormone analog, a melanin concentrating hormone antagonist, the OB protein, a leptin analog, a galanin antagonist and an orexin receptor antagonist.

43. A kit as defined in claim 42 wherein said anorectic agent is phentermine.

44. A kit as defined in claim 42 wherein said monoamine reuptake inhibitor is sibutramine, said serotoninergic agent is dexfenfluramine or fenfluramine, and said dopamine agonist is bromocriptine.

45. A kit as defined in claim 41 wherein said lipase inhibitor is tetrahydrolipstatin.

* * * * *